United States Patent [19]

Huszar

[11] Patent Number: 5,897,988
[45] Date of Patent: Apr. 27, 1999

[54] PROCESS AND SYSTEM FOR SELECTION OF MATURE SPERM BY SURFACE MEMBRANE DETERMINANTS FOR ASSISTED REPRODUCTION

[75] Inventor: Gabor B. Huszar, Woodbridge, Conn.

[73] Assignee: Yale University, New Haven, Conn.

[21] Appl. No.: 09/010,247

[22] Filed: Jan. 21, 1998

[51] Int. Cl.$^6$ ..................................................... A01N 1/02
[52] U.S. Cl. ............................................................... 435/2
[58] Field of Search ................................. 435/2; 530/852

[56] References Cited

U.S. PATENT DOCUMENTS

| | | | |
|---|---|---|---|
| 4,582,865 | 4/1986 | Balazs et al. | 524/29 |
| 4,804,537 | 2/1989 | Bergman et al. | 424/105 |
| 4,945,044 | 7/1990 | Huszar | 435/17 |
| 5,616,568 | 4/1997 | Pouyani et al. | 514/54 |
| 5,672,336 | 9/1997 | Sharma | 424/45 |
| 5,674,511 | 10/1997 | Kacher et al. | 424/401 |

OTHER PUBLICATIONS

Huszar et al. Hylan–Tantalum gel selectively binds sperm fractions with improved viability and morphology. The American Fertility Society, 50th Annual Meeting, 1994.

Hans et al. Selection of motile or immotile sperm by hylan–tantalum gel: Creatine kinase (CK) and aniline blue staining patterns. The 7th International symposium on Spermatology, Cairns, Australia, 1994.

Palermo et al. Intracytoplasmic sperm injection: a powerful toll to overcome fertilization failure. Fertility and Sterility vol. 65 pp. 899–908, 1996.

Sperm Plasma Membrane Remodeling During Spermiogenetics Maturation in Men: Relationship Among Plasma Membrane β1, 4–Galactosyltransferase, Cytoplasmic Creatine Phosphokinase and Creatine Phosphokinase Isoform Ratios,, Biology of Reproduction 56, 1020–1024 (1997) by Gabor Huszar, Marco Sbracia, Lynne Vigue, David J. Miller and Barry D. Shur.

Hyaluronic Acid (Sperm Select) Improves Retention of Sperm Motility and Velocity in Normospermic and Oligospermic Specimens, Fertility and Sterility, vol. 54, No. 6, Dec. 1990. by Gabor Huszar, M.D.., Melani Willets, M.S., and Marcelia Corrales, M.D.

Sperm Creatine Phosphokinase M–isoform ratios and Fertilizing Potential of Men: A Blinded Study of 84 Couples Treated With In–Vitro Fertilization, by Gabor Huszar, M.D., Lynne Vigue, M.S. and Mahomood Morshedi, M.D. Fertility and Sterility , vol. 57, No. 4, Apr. 1992

The Regulation of Sperm Motility by a Novel Hyaluronan Receptor, Fertility and Sterility, vol. 61, No. 5, May , 1964; by Barbara S. Kornovski, D.Sc., John McCoshen, Ph.D, Jeremy Kredester, M.D. and Eva Turley, Ph.D.

Aniline Blue Staining As A Marker of Sperm Chromatin Defects Associated With Different Semen Characteristics Discriminates Between Proven Fertile and Suspected Infertile Men, International Journal of Andrology, 1990,13, pp. 452–462, by J. Auger, m. Mesbach, C. Huber and J.P. Dadoune, Biology of Fertility and Cytogenetics Laboratory, CECOS, Hospital Hotel–Dieu and Medical Statistics Laboratory, Rene Descartes University, Paris, France.

Ezzell, C. Picking A Ripe One: A New Strategy For Selecting Sperm The Journal of NIH Research, Feb., 1997, vol. 9, No. 2.

Spermatogenesis–Related Change In The Synthesis Of The Creatine Kinase B–Type and M–Type Isoforms in Human Spermatozoa, Molecular Reproduction and Development, 25:258–262, 1990; by Gabor Huszar and Lynne Vigue; The Sperm Physiology Laboratory, Department of Obstetrics and Gynecology, Yale University School of Medicine, New Haven, Connecticut.

Evidence for Presence of Hyaluronan Binding Protein on Spermatozoa and Its Possible Involvement in Sperm Function; Molecular Reproduction and Development, 38:69–76, 1994. by Sripriya Ranganathan, Amit Kumar Ganguly and Kasturi Datta, Biochemistry Laboratory, School of environment Sciences, Jawaharlal Nhru University, New Delhi, India.

*Primary Examiner*—George C. Elliott
*Assistant Examiner*—John S. Brusca
*Attorney, Agent, or Firm*—DeLio & Peterson, LLC

[57] ABSTRACT

A process and system for selecting mature sperm for assisted reproduction techniques such as intracytoplasmic sperm injection comprises applying a binding substrate specific to mature sperm to a surface; applying a sperm suspension to the surface; and contacting the sperm suspension and the mature sperm binding substrate on the surface. The process then comprises permitting mature sperm from the sperm suspension to bind to the mature sperm binding substrate at a periphery thereof; and removing bound sperm from the periphery of the mature sperm binding substrate. Preferably, the mature sperm binding substrate is a fluid and comprises hyaluronic acid or a salt thereof, a polysaccharide, a glycosaminoglycan, a zona pellucida component, zona protein of the egg membrane or a structural or functional homolog or analog of the sperm-binding elements of the female reproductive tract or the zona pellucida, a proteoglycan, or an antibody to a protein receptor for mature sperm.

70 Claims, 7 Drawing Sheets

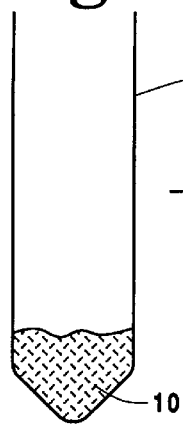
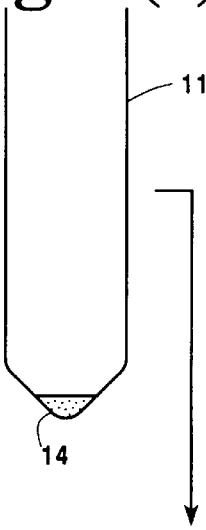
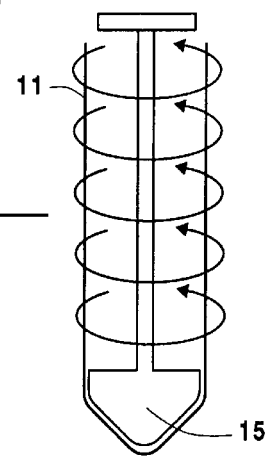
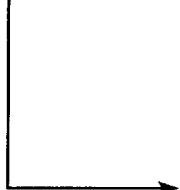
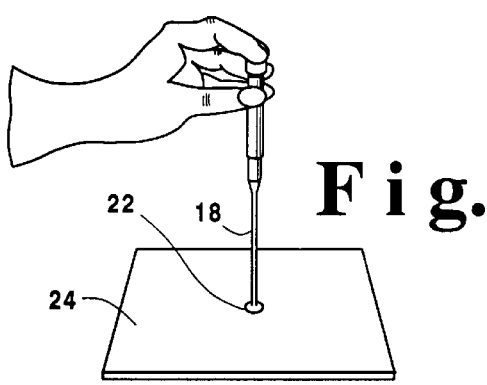
Fig. 1(a) Fig. 1(b) Fig. 1(c) Fig. 1(d) Fig. 1(e) Fig. 1(f) Fig. 1(g)

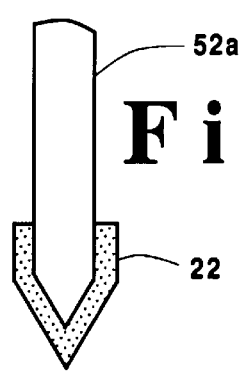
Fig. 10
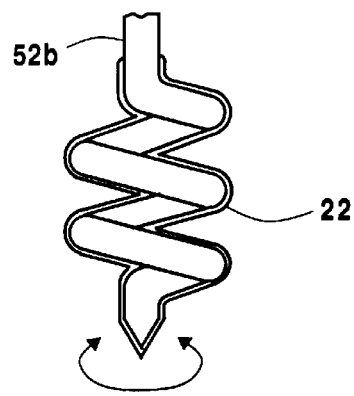
Fig. 11
Fig. 12
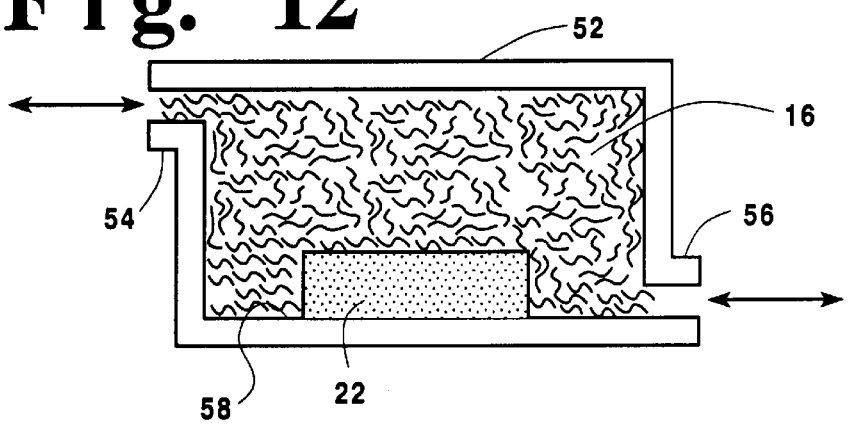
Fig. 14
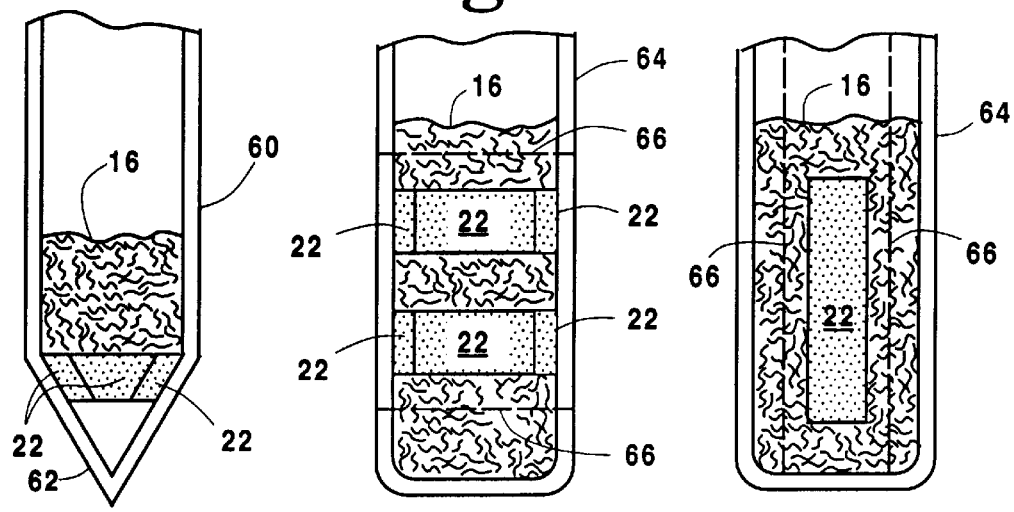
Fig. 13
Fig. 15

PROCESS AND SYSTEM FOR SELECTION OF MATURE SPERM BY SURFACE MEMBRANE DETERMINANTS FOR ASSISTED REPRODUCTION

BACKGROUND OF THE INVENTION

1. Field of the Invention

The present invention relates to a process and system for selecting mature sperm from a sperm population for assisted reproduction, and for intracytoplasmic sperm injection (ICSI) and determining mature sperm count and, in particular, to the use of a mature sperm binding substrate applied to a surface on which mature sperm, but no sperm with diminished maturity, selectively bind. The mature sperm binding substrate will also serve as laboratory testing material to determine whether some fertile or infertile men have a sperm maturation deficiency.

2. Description of Related Art

Assisted reproduction techniques in current use include intrauterine insemination of sperm, in vitro fertilization (IVF) of the egg with sperm, and ICSI and spermatid or other immature germ cell injection into oocytes. In the case of intrauterine insemination and conventional IVF, assisting the sperm selection process is not necessary, because the fertilization depends on a selection process that is based on physiological and specific interaction of sperm and oocyte. However, in severe male infertility requiring ICSI with ejaculated, epididymal or testicular sperm, the operator arbitrarily chooses and introduces the fertilizing male gamete regardless the maturity of the sperm.

In the ICSI process, the operator injects the sperm into the oocyte, thus overriding the steps of sperm-zona interaction which in conventional fertilization with mature sperm consists of the following steps: sperm-zona pellucida binding acrosome reaction of the spermatozoa, sperm penetration into the zona, fusion of the sperm and the oolemma, oocyte activation and creation of an embryo. Immature sperm do not bind to the zona because the development of the zona-binding site is part of the sperm maturation process. In the present ICSI procedure the operator may select both mature or immature spermatozoa. Immature spermatozoa, which have a higher incidence of faulty genetic material, and which prior to ICSI have never been part of the fertilization pool, will undoubtedly cause at least a portion of the pregnancies resulting from the ICSI process.

At the present time, the overt rate of congenital malformations and sex chromosome abnormalities in humans, although it is about double of the normally occurring rate, it is still very low in ICSI offspring. However, the oldest of these children are only a few years old, and thus it is not yet known if their individual development, growth, sexual maturation, fertility, cancer rate, life span and the rate of congenital malformation in their children are affected. An important goal would be to develop methods by which mature sperm, similar to those predominant in normal fertile men, whether arising from ejaculated semen, from the epididymis or testes, could be selected for ICSI. Such sperm selection process would maintain the risk of adverse fetal outcome at a level similar to that of couples reproducing by conventional methods based on sperm-oocyte interaction. Ideally, the selection technique would be able to select both motile and immotile mature sperm. A selection technique specific for mature sperm would also facilitate the determination of the proportion of mature sperm in husbands of infertile couples, in order to test male fertilization potential and determine the necessity and optimal choice among the available methods of assisted reproduction.

Bearing in mind the problems and deficiencies of the prior art, it is therefore an object of the present invention to provide a method and system for distinguishing and selecting mature sperm from immature sperm.

It is another object of the present invention to provide a method and system for selecting mature sperm in which the motility indicates viability and is also able to select immotile but viable mature sperm. Non-viable sperm, because the integrity of the oocyte activator factor(s) and genetic material are diminished, are not desirable for ICSI.

A further object of the invention is to provide a method and system for selecting mature sperm which may be used in assisted reproduction techniques, particularly the ICSI method.

It is yet another object of the present invention to provide a testing method and system for determining mature sperm count in general sperm population men who are investigated for potential diminished fertility or infertility.

Still other objects and advantages of the invention will in part be obvious and will in part be apparent from the specification.

SUMMARY OF THE INVENTION

The above and other objects, which will be apparent to those skilled in the art, are achieved in the present invention which relates, in a first aspect, to a process for selecting mature sperm comprising the steps of applying a binding substrate specific to mature sperm to a surface; applying a sperm suspension to the surface; and contacting the sperm suspension and the mature sperm binding substrate on the surface. The process then comprises permitting mature sperm from the sperm suspension to bind to the mature sperm binding substrate at a periphery thereof; and removing bound sperm from the periphery of the mature sperm binding substrate.

In a related aspect, the present invention provides a process for selecting mature sperm comprising the steps of contacting a sperm suspension and a binding substrate specific to mature sperm; permitting mature sperm from the sperm suspension to bind to the mature sperm binding substrate at a periphery thereof; immobilizing the mature sperm bound to the mature sperm binding substrate; and removing bound sperm from the periphery of the mature sperm binding substrate.

Preferably, the mature sperm binding substrate is a fluid and comprises hyaluronic acid or a salt thereof, a polysaccharide, a glycosaminoglycan, a zona pellucida component, zona protein 2 of the egg membrane or a structural or functional homolog or analog of the sperm-binding elements of the female reproductive tract or the zona pellucida, a proteoglycan, or an antibody to a protein receptor for mature sperm.

The mature sperm binding substrate is more preferably selected from the group consisting of hyaluronic acid or a salt thereof, a polysaccharide, a glycosaminoglycan, a component of zona pellucida or sperm-binding proteins arising from the oocyte, a proteoglycan, and an antibody to a protein receptor for mature sperm.

The mature sperm binding substrate is not specific to immature sperm. In the preferred embodiment, the sperm suspension and the mature sperm binding substrate are applied and contacted on the surface of a structure transparent to the wavelength of light energy of the visualization system, for example, on the surface of a glass slide, such that both motile and non-motile mature sperm bind to the mature sperm binding substrate. The process may further include the step of viewing the mature sperm bound to the mature sperm binding substrate by passing light through the transparent structure and the mature sperm binding substrate on the surface. The mature sperm may be removed from the mature sperm binding substrate by a micropipette.

The process may further include the step of agitating the sperm suspension with respect to the mature sperm binding substrate on the surface, and waiting a predetermined time to permit a portion of mature sperm bound to the mature sperm binding substrate to disbond from the mature sperm binding substrate. The process may also include the step of immobilizing the mature sperm bound to the mature sperm binding substrate, by using a micropipette to crush or at least partially remove tails of the mature sperm. The process also optionally includes the steps of determining relative tail motion and activity of sperm bound to the binding substrate and selecting for removal bound sperm having greater tail motion and activity.

The process may further include washing the mature sperm removed from the mature sperm binding substrate; and injecting the washed sperm into an egg to attempt to fertilize the egg. The sperm may comprise human sperm or non-human mammalian sperm, including those of wild animals existing in zoos and of endangered species.

In another aspect, the present invention provides a system for selecting mature sperm comprising a surface having coated on a portion thereof a mature sperm binding substrate, the surface adapted to receive a sperm suspension for contacting the mature sperm binding substrate and selectively binding mature sperm to the mature sperm binding substrate; and means for removing the sperm bound to the mature sperm receptor fluid.

The present invention also relates to a system for selecting mature sperm comprising means for receiving a coating of a mature sperm binding substrate, the receiving means adapted to receive a sperm suspension for contacting the mature sperm binding substrate and selectively binding mature sperm to the mature sperm binding substrate; and means for removing the sperm bound to the mature sperm receptor fluid.

Preferably, the removing means comprises a micropipette. The system may further include a micropipette for injecting removed mature sperm into an oocyte, the micropipette for removing the mature sperm having a larger diameter than the micropipette for injecting the removed mature sperm.

The receiving means may comprise a transparent structure on which the sperm suspension and the mature sperm binding substrate are contacted, such as a glass slide. The glass slide may have a depression therein for receiving the sperm suspension and the mature sperm binding substrate.

The system receiving means may also comprise a projection on which the mature sperm binding substrate is at least partially coated, wherein the projection is straight or helical. The projection may be frangible to permit at least a portion of the coated projection to be broken off the remaining structure and manipulated to remove mature sperm. The receiving means may also comprise a three dimensional structure to facilitate observation of multiple bound mature sperm.

The receiving means may further comprise a container having the mature sperm binding substrate coated on an inner surface thereof, and further including means for agitating the sperm suspension with respect to the mature sperm binding substrate. The container may have the mature sperm binding substrate coated in a strip on an inner surface thereof. The receiving means may also comprise a mesh having the mature sperm binding substrate coated on at least a portion thereof, or a round structure having the mature sperm binding substrate coated on at least a portion of an outer surface thereof.

In yet another aspect, the present invention provides a process for determining the proportion of mature sperm in a sperm sample comprising the steps of applying a mature sperm binding substrate to a surface; applying a sperm suspension of known concentration from the sperm sample to the surface; contacting the mature sperm binding substrate and the sperm suspension on the surface; permitting mature sperm from the sperm suspension to bind to the mature sperm binding substrate at a periphery thereof; and determining the proportion of mature sperm from the sperm suspension bound to the mature sperm binding substrate. The process may further include the step of contacting the mature sperm bound to the mature sperm binding substrate with a toxin to the mature sperm.

The process also may include the steps of determining if a predetermined minimum proportion of mature sperm is present in the sample, determining if the donor of the sperm sample is suitable for assisted reproduction procedures, and the step of determining the most suitable assisted reproduction technique for the donor based on the proportion of mature sperm present in the sample.

In a further related aspect, the present invention provides a system for determining the proportion of mature sperm in a sperm sample comprising a surface having coated on a portion thereof a mature sperm binding substrate, the substrate adapted to receive a sperm suspension for contacting the mature sperm binding substrate and selectively binding mature sperm to the mature sperm binding substrate; and means for determining proportion of the sperm bound to the mature sperm binding substrate. The determining means may comprise a microscope and a video system for analysis of sperm tail dynamics.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIGS. 1(a) to 1(g) are composite schematic illustrations of sperm sample preparation technique for the present invention.

FIG. 10 is a close-up of one type of straight projection used in the system of FIG. 9.

FIG. 11 is a close-up of one type of helical projection used in the system of FIG. 9.

FIG. 12 is a vertical sectional view of another system having a container in which may be applied the mature sperm binding substrate and which permits the sperm suspension to be agitated while contacting the substrate.

FIG. 13 is a vertical sectional view of yet another system having a container in which may be coated on an inner surface the mature sperm binding substrate to contact the sperm suspension.

FIG. 14 is a variation of the system of FIG. 13.

FIG. 15 is another variation of the system of FIG. 13.

DESCRIPTION OF THE PREFERRED EMBODIMENT(S)

Figure 2:
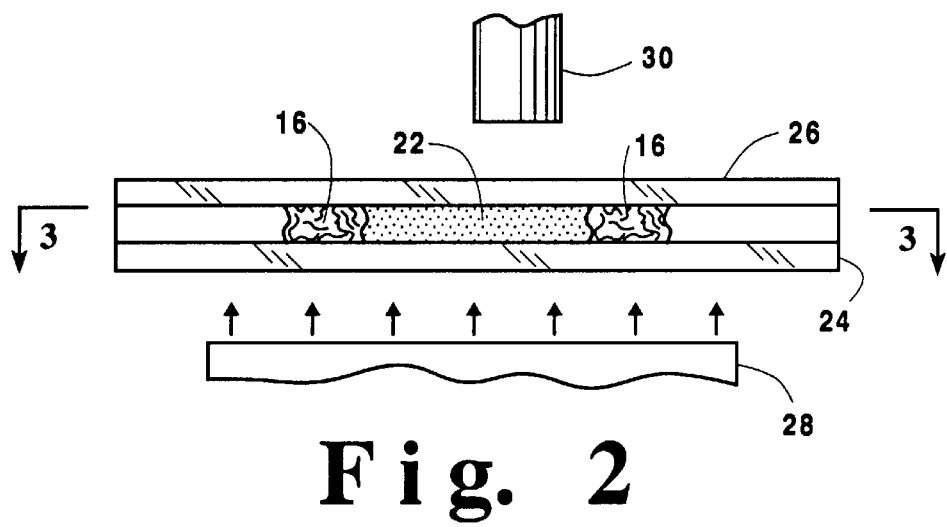
FIG. 2 is a vertical sectional view of a transparent slide system on which may be viewed the mature sperm binding substrate contacting the sperm suspension.

In describing the preferred embodiment of the present invention, reference will be made herein to FIGS. 1–20 of the drawings in which like numerals refer to like features of the invention. Features of the invention are not necessarily shown to scale in the drawings.

In assessing male fertility, research in the past few years has focused upon the relationship between sperm maturity and sperm function. Two objective biochemical markers of sperm maturity have been developed: a) sperm CK concentration which reflects the completion of cytoplasmic extrusion during sperm maturation; and b) a sperm maturation related change of CK-isoform expression from the B-type to the M-type. The CK markers are predictive for male fertility and infertility. In a blinded study of 84 couples treated with IVF in 1990, the predictive rate of CK-M ratio [%CK–M/ (CK–M+CK–B)] for pregnancies was 30.4% per cycle.

In following up the reasons underlying these prediction rates, it was discovered that immature sperm with cytoplasmic retention did not bind to the oocyte. It has been determined that, along with cytoplasmic extrusion and the commencement of the CK-M isoform synthesis, a sperm plasma membrane remodeling also occurs during spermiogenesis which is the last phase of spermatogenesis.

The present invention is based on the discovery of development-related remodeling of spermatozoa which occurs both within the cell and simultaneously on the sperm surface membrane. As a result, it has been found that mature and immature sperm may be distinguished from each other based on their surface membrane properties. Also, the structure of the surface membrane then predicts the degree of sperm maturity within the cytoplasmic compartment. Selected substrates for which the mature sperm, but not the immature sperm, have receptors provide a vehicle for efficient selection of mature and viable spermatozoa which is particularly suitable for use with the aforementioned ICSI process for both human and domestic and wildlife animal reproduction. Some of the proposed mature sperm binding materials, such as hyaluronic acid, proteoglycans and polysaccharides are common for all species, however the sperm-binding components of the zona pellucida or their structural or functional homologs and analogs will be species specific, as the sperm-zona interaction is species specific. The present invention permits mature sperm, similar to those predominant in normal fertile men, whether arising from ejaculated semen or from the epididymis, or testes, to be selected for ICSI in order to maintain the risk of adverse fetal outcome to that of the population reproducing by conventional methods based on sperm-oocyte interaction. The mature sperm selected in accordance with the present invention may also be utilized in other assisted reproduction techniques discussed previously, such as intrauterine insemination and IVF.

Based on data regarding sperm maturity and sperm function, the present invention is most useful for the selection of mature human sperm for ICSI fertilization procedures. The techniques used in the present invention are non-invasive and also applicable to viable sperm of diminished motility.

The preferred mature sperm binding substrate has been found to be Hylan, a complex of hyaluronic acid (HA), which is a naturally occurring component of the female reproductive tract which surrounds the oocyte. Both hyaluronic acid and salts thereof, such as hyaluronic acid conjugates with proteins, glycosaminoglycans or inorganic agents, are useful as the mature sperm binding substrate. The production of hyaluronic acid and its salts in a gel form is described in U.S. Pat. No. 4,582,865, the disclosure of which is hereby incorporated by reference. Hylan is available from Biometric, Inc., Ridgefield, N.J. The appearance of the HA receptor on the external mature sperm membrane is apparently/believed to be part of the sperm developmental membrane remodeling. Because immature or non-viable sperm do not bind to HA, the selection of bound sperm is important improvement for ICSI. Due to the act that HA is a physiologically occurring component of the cumulus, there should be no ethical concerns about its use. In the practice of in vitro fertilization and ICSI.

Other binding substrates which are specific to mature, but not immature, sperm are polysaccharides, glycosaminoglycam and proteoglycans, for example mannose. Also, a binding substrate made from material similar or identical to the naturally occurring zona pelludica of, for example, human or non-human mammalian eggs, such as monkey eggs. Such zona pelludica proteins may be extracted from unfertilized human or monkey oocytes or may be synthesized in the laboratory by chemical, biological or genetic engineering processes. Zona protein from other mammalian species may be used for ICSI procedures involving reproduction of those species. The present invention is particularly useful for reproduction of mammalian species which are confined to zoos or endangered, which may otherwise not be easily reproduced by assisted reproduction techniques.

The present invention also provides for the ICSI and other assisted reproduction processes viable sperm which have completed the cellular maturation process, whether or not the sperm are motile. In the case of immotile and viable mature sperm, the sperm membrane integrity is maintained. This is important because the viability of non-motile sperm can not be assuredly established with presently known non-invasive methods. In prior art procedures, non-motile viable sperm have been identified with motility-inducing drugs, which may have an adverse effect on the fertilization process or on the developing mbryo. Because the HA or other binding substrate receptor apparently appears only on the viable mature sperm and disappears when the viability is diminished, as shown by the vital staining of the HA bead-bound sperm, the use of such coatings on surfaces have been found to be ideal for the selection of mature and viable spermatozoa for ICSI.

Additionally, by use of the Hylan or other mature sperm binding substrate coating, there is facilitated the selection of mature, viable spermatozoa which also have improved genetic material. In recent ongoing studies with fluorescent in situ hybridization, using probes for chromosomes X, Y, 10, 11 and 17, it has been demonstrated increased frequency of disomy and diploidy in sperm fractions with diminished maturity CK parameters. Mature sperm, however, have been found to have a very low incidence of cytoplasmic retention or immature chromatin. Immature sperm, due to the cytoplasmic retention, also show a higher rate of lipid peroxidation which causes DNA cleavage and potential increases in childhood cancer rates of the offspring. The establishment of the remodeling step affirms that immature sperm populations with lack of the spermiogenetic membrane remodeling, which provide the zona pellucida binding site (s), have never participated in oocyte fertilization until ICSI became available.

In performing the process of the present invention, it has also been found that applying the mature sperm binding substrate in a fluid form (e.g., gel or liquid) to the surface of a solid structure facilitates the detection and removal of mature sperm which become bound to a periphery of the binding substrate.

The coating of mature sperm binding substrate on the structural surface is contacted with a washed or unwashed sperm suspension which is applied around the surface at a periphery of the binding substrate. In preparing the sperm sample, i.e., liquifaction after ejaculation, after a waiting time of ten (10) to thirty (30) minutes at 36° C. the sperm concentration and motility are checked. If the semen is less than 100 microliters in volume, the suspension is diluted with human tubal fluid with albumine until it reaches a volume of 400 microliters. A standard counting procedure utilizing a Makler chamber, or similar device, under a microscope with a phase contrast lens is applied to determine the total amount of sperm and the total amount of motile sperm.

In the case where there are no motile sperm and less than 200,000 total sperm in the sperm suspension, the sample is preferably centrifuged in a conical shaped test tube, appropriate for the volume of sperm, in order to concentrate the available sperm and remove it from the remaining liquid. If there are no motile sperm and total sperm, is more than 200,000, centrifugation is not necessary. Once the sperm has been collected, it is diluted, if necessary, to a volume of approximately 100–200 microliters. Optimally, the concentration of sperm will be in the range of about 2,000 to 5,000 sperm per microliter, and further dilution, centrifugation and resuspension may be performed to achieve this concentration. The dilution/resuspension fluid is preferably an isotonic medium such as human tubal fluid with albumin or similar, or any generally used preferred medium of choice in the user's, or operator's laboratory.

If the sperm sample contains motile sperm and the sperm count is less than 10,000,000 (ten million) sperm per milliliter, a concentration step based on centrifugation and resuspension may be performed, or the sperm selection may be performed using the neat semen. If the sperm count is greater than 10,000,000 (ten million) sperm per milliliter, the sperm may be selected from the neat semen without the concentration step.

As shown in FIG. 1, the sperm suspension sample preparation includes (a) obtaining and preparing a sperm sample 10 in a test tube or vial 11, (b) adding to the sample a sperm washing solution 12 while agitating and (c) concentrating the wash sample by centrifugation to obtain a sperm pellet 14. A resuspending solution is then added to the pellet and (d) the sperm pellet is resuspended and agitated with a stirrer. A pipette 18 is used to take an aliquot of the sperm suspension 20 which is then (g) deposited on an embodiment of the invention 24 in order to make contact with a surface coated with the mature sperm binding substrate 22.

The sperm suspension is applied as a coating to all or a portion of the desired structure surface which contains a coating of the mature sperm binding substrate. Alternatively, the sperm solution may be first applied to the surface and then the coating of binding substrate applied. The binding substrate and sperm suspension are contacted along the periphery of the binding substrate fluid for a suitable time, depending on the sperm concentration, motility and velocity. The sperm suspension may be agitated with respect to the mature sperm binding substrate in order to effect contact between the sperm and the binding substrate. Typically, a time of 1 to 20 minutes is given to permit the mature sperm to bind to the mature sperm binding substrate. This amount of time also permits any mature sperm which lose their viability (and thus would not be a good candidate for the ICSI procedure) to disbond from the mature sperm binding substrate. Preferably, a waiting time of at least 5 to 10 minutes is utilized to assure viability of the sperm attached to the binding substrate.

The preferred surface on which the mature sperm binding substrate and sperm solution are applied and contacted is a transparent solid, such as a glass slide. Such a surface is shown in FIG. 1. In addition to a glass slide surface, other surfaces such as polycarbonate, may be utilized in order to effect optimal contact between the mature sperm binding substrate and the sperm suspension.

Figure 3:
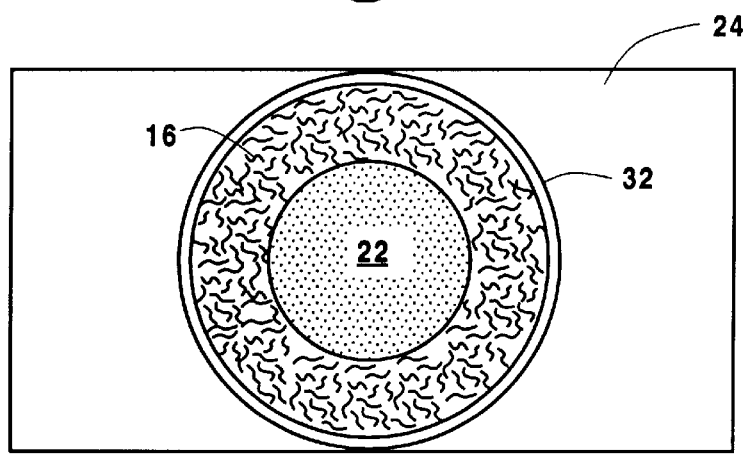
FIG. 3 is a top plan view of the transparent slide system of FIG. 2.

As shown in FIGS. 2 and 3, the preferred structure 24 comprises a transparent structure such as a glass slide, on the surface of which is deposited the mature sperm binding substrate 22 and, surrounding substrate 22 and in contact therewith, the sperm suspension 16. To contain the sperm suspension in a designated area in close proximity to substrate 22, a grease pencil mark 32 may be made initially on glass slide 24 (FIG. 3). As shown in FIG. 2, a transparent glass slide cover 26 is disposed over the transparent glass slide 24, sandwiching the binding substrate 22 and surrounding sperm suspension between. A microscope 30 (optionally including a video system) utilizing a lower light source 28, may then be utilized to view the interface between the binding substrate 22 and sperm suspension 16 and determine which, if any, sperm bind to the binding substrate 22.

Figure 4:
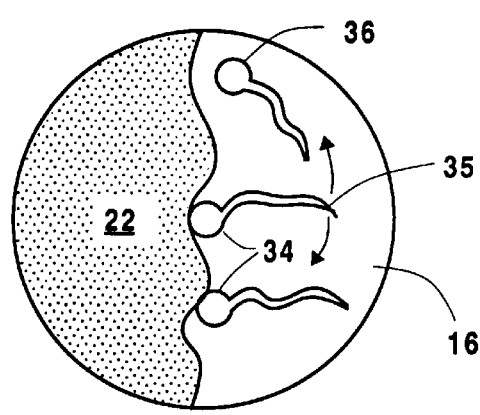
FIG. 4 is a close-up view of mature sperm binding to the binding substrate of FIG. 3.
Figure 5:
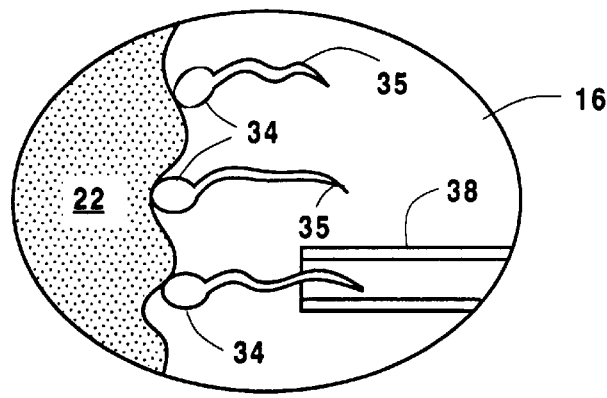
FIG. 5 is a close-up view of bound mature sperm of FIG. 4 being immobilized.

As shown in FIGS. 4 and 5, mature sperm 34 will bind to the binding substrate 22 whereas immature, non viable sperm 36 will not. Some of the mature sperm 34 are motile, as will be indicated by the movement of side-to-side sperm tail 35, whereas other mature sperm bound to the substrate 22 may be nonmotile. In the case of the latter, it is preferable to agitate the sperm suspension with respect to the binding substrate so as to provide an opportunity for immotile sperm to contact the binding substrate 22 and bind therewith.

As shown more clearly in FIG. 5, a micropipette 38 may be utilized to gently crush or partially remove sperm tail 35 and then remove the mature sperm itself bound to the substrate 22.

Figure 6:
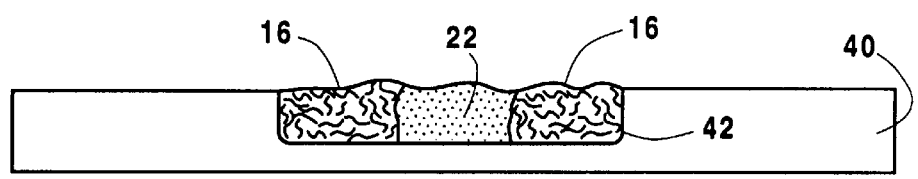
FIG. 6 is a vertical sectional view of an alternate transparent slide system having a depression for receiving the mature sperm binding substrate and the sperm suspension.

The present invention also contemplates utilizing other structures and surfaces on which the binding substrate 22 and sperm suspension 16 may be contacted. In FIG. 6, for example, a transparent glass slide 40 contains a well 42 in which are applied binding substrate 22 and sperm suspension 16 as coating to the bottom of the well.

Figure 7:
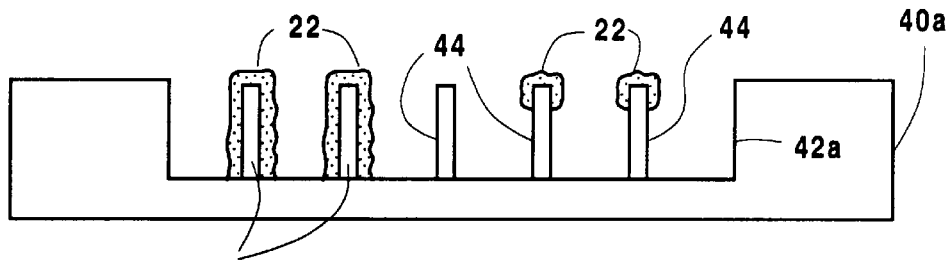
FIG. 7 is a vertical sectional view of a modification of the transparent slide system of FIG. 6 having projections in the depression for receiving the mature sperm binding substrate.

FIG. 7 depicts a modification of the well structure of FIG. 6, further including a plurality of upward projections 44 in well 42a of slide 40a on which are coated binding substrate 22. In the projections shown to the left in well 42a, the binding substrate may be coated over the entirety of the projection 44 (which may be in the form of a spike or plate), whereas in the projections shown on the right side of well 42a, the binding substrate 22 is coated on the surface of only the tips of the projections.

Figures 8, 9:
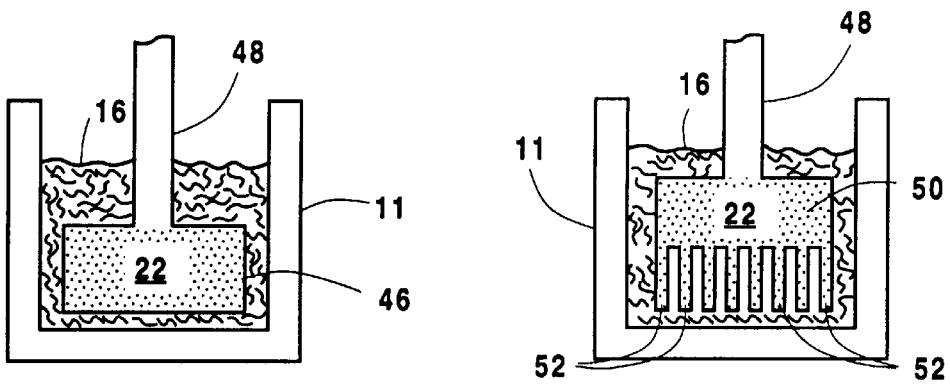
FIG. 8 is a vertical sectional view of an alternate system for receiving the mature sperm binding substrate on a paddle in a container.
FIG. 9 is a vertical sectional view of a modification of the system of FIG. 8 having projections on the paddle for receiving the mature sperm binding substrate.

In FIGS. 8 and 9, a variation of the invention is demonstrated wherein the binding substrate 22 is coated on the surface of a flat paddle 46 which is suspended by handle 48 in a sperm suspension 16 contained within test tube 11. In FIG. 9, a similar paddle 50 contains a coating of binding substrate 22, except that this paddle includes plurality of downward projections 52 on which the coating is also applied and suspended within sperm suspension 16. Variations on the projections of FIG. 9 are shown in FIGS. 10 and 11. In FIG. 10, a spike shaped projection 52a contains a binding substrate coating 22 only on the surface thereof and in FIG. 11 a helical or coil shaped projection 52b contains binding substrate coating 22 on the entire lower surface thereof. As a separate surface for coating the binding substrate 22, coiled projection 52b may be rotated in the direction shown by the arrow to provide agitation with respect to the sperm suspension which it is placed.

To provide further agitation to attract nonmotile, mature sperm, a container 52 (FIG. 12) may have deposited on a lower inner surface 58 the coating of binding substrate 22. The sperm suspension 16 may then be introduced through inlet/outlet 54 and inlet/outlet 56 and periodically pumped in and out through one or both of the outlets to provide agitation with respect to binding substrate 22.

The binding substrate 22 may be coated onto the inner surface of a centrifuge tube or other container 60, as shown in FIGS. 13, 14 and 15. In FIG. 13, a test tube 60 containing a conical lower end 62 has coated therein the binder substrate 22. Sperm suspension 16 is then placed in the container in order to contact the binder substrate 22. In FIG. 14, a pair of horizontal strips of binder substrates 22 are placed within the lower end of container 64. After allowing mature sperm from suspension 16 to contact and bind to substrate 22, the container 64 may be cut along lines 66 and opened up to facilitate viewing and removal of mature sperm bound to substrate 22. A variation of this is shown in FIG. 15, wherein binding substrate 22 is applied as a vertical strip on the inner wall of container 64, and cut line 66 is used to remove the substrate 22 after sperm from suspension 16 has had mature sperm bound to it.

Figure 16:
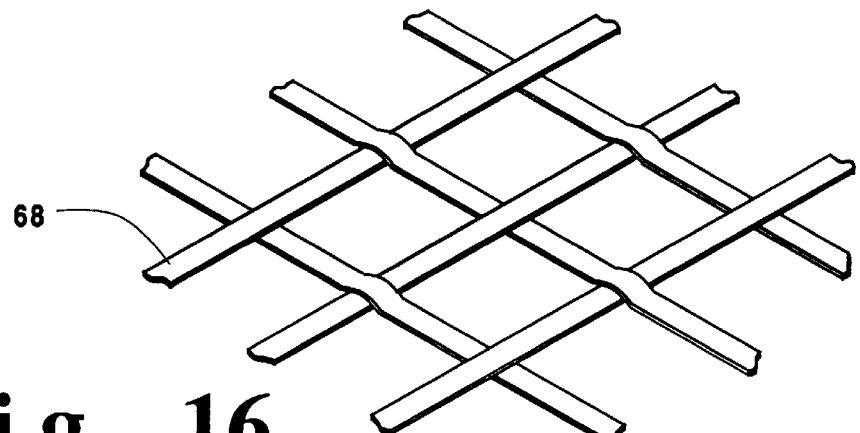
FIG. 16 is a perspective view of a mesh on which may be coated the mature sperm binding substrate of the present invention.
Figure 17:
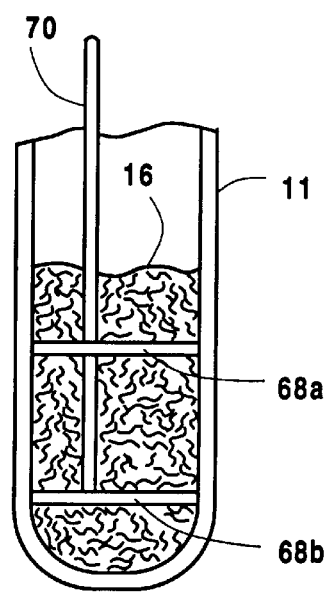
FIG. 17 is a vertical sectional view of a container having therein the mesh of FIG. 16 for contacting the sperm suspension.

A further embodiment is shown in FIGS. 16 and 17, wherein a mesh 68 of a transparent or thin metallic, or other sieve material is coated with binding substrate 22. One or more of these coated mesh segments may be connected by handle structure 70 and immersed within a fluid suspension 16 held within container 11 in order to attract mature sperm to the binding substrate on the surface of mesh 68a, and 68b.

Figure 18:
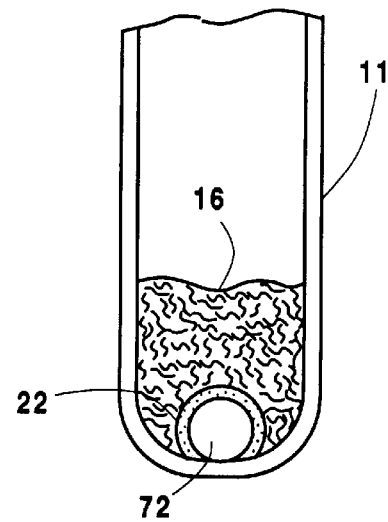
FIG. 18 is a vertical sectional view of a container having therein a round structure coated with sperm binding substrate for contacting the sperm suspension.

Yet another embodiment of the invention is shown in FIG. 18, wherein a round, three-dimensional structure, specifically a glass sphere 72, is coated with a binder substrate 22 and immersed within sperm suspension and container 11. The container 11 may then be moved in the direction indicated by the arrow to cause movement of the coated glass sphere 72 for agitation to attract nonmotile, mature sperm to the binder substrate 22 surface. All these embodiments are designed to optimal concentration of sperm and exposure of sperm to the mature sperm binding protein with the highest efficiency possible, given the semen volume and sperm concentration therein. For instance, in the tube vessel of FIG. 14, depending on the semen volume or resuspension fluid volume, the lower or higher ring (of both) may be utilized to attract sperm, depending on the volume which contains the mature sperm.

After a time sufficient for the mature and immature sperm in the suspension to pass in the vicinity of the binding substrate, mature sperm become selectively bound to the binding substrate, while immature sperm do not. Agitation may be used to improve contact between the sperm in the suspension and the binding substrate, particularly to encourage binding of immotile, mature sperm which are still useful for fertilization. Because in mature sperm, along with the spermiogenetic remodeling of sperm plasma membrane, there is also an expression of receptors for HA and the other aforementioned binding substrates, the mature sperm binding substrate facilitates the selection of mature, viable spermatozoa for ICSI, independently from the presence of sperm motility.

The binding of mature sperm may be viewed by a light microscope at approximately 100X magnification. If the number of motile sperm is less than 10% of the sperm population, or if the percent of motile sperm is declining with time, one may use more than one aliquotes of sperm on more than one surface. If the sperm is completely nonmotile, an aliquote should be tested with a viability stain to assess viability, such as FertiLite (Molecular Probes, Inc., Eugene Oregon), or similar.

In case of embodiments of vertical nature, for instance, FIGS. 7, 8, 9 and 10, the structures with the bound sperm will have to be converted into a horizontal position in order to be observable under standard microscopic conditions. This may be done by making the projections frangible, so that they may be broken off at their base. With respect to enclosed chambers, such as depicted in FIG. 12, the integrity of these structures will have to be broken to make the bound mature sperm accessible and observable.

Motile, mature sperm, upon attachment to the mature sperm binding substrate such as HA increases their cross-beat frequency of the sperm tail to a frequency greater than 15 Hertz. Integrity and viability is reflective of maintenance of attachment and motion, as it was shown by the enhanced retention of motility and velocity in solution. Some mature, marginally motile sperm have been seen to increase tail cross-beat frequency upon attachment to the sperm binding substrate.

Another functionally important testing aspect, in addition to the cross-beat frequency, is that the pattern, kinematic analysis, relaxation pattern and beat-wave pattern of the sperm tail as it responds to the mature sperm binding material may have diagnostic utility. The motion analysis of the real-time or videotaped activity of the sperm tail may be incorporated in the diagnostic procedure assessing sperm maturity using a computer-assisted semen analysis system.

Another advantage of the technology is that the sperm which are bound to the binding substrate are immobilized with respect to forward motion, but not by tail beating. As used herein, the term "immobilized" refers to reducing the forward mobility of the mature sperm so that it is easier to remove them and handle in subsequent procedures. Eliminating tail beating is done by gently touching or crushing the sperm tail. Alternatively, a part of the tail of the bound sperm may be removed by breaking off with a micropipette. Another advantage of the sperm binding is that the sperm may be captured easier and the operator does not need the presently used high viscosity PVP (polyvinylpyrrolidone) in order to diminish sperm velocity.

Thereafter, the bound sperm are washed by the IVF medium of choice with a micropipette, and/or sperm may be placed in a microdrop or medium after removal. The mature sperm may be more easily removed from the binding substrate by use of a pipette which is wider than that used for injection. Preferably, the pipette may be from about 7 to 10 microns in diameters. Thereafter, the collected mature sperm are washed in a micro-drop of medium and may then be employed for fertilization by microinjection in the ICSI or any other assisted reproductive techniques by well-known methods by using a pipette of 4–8 microns in diameter.

The present invention may also be utilized analytically to test for and provide an assessment of sperm maturity and male fertility, to determine the most appropriate assisted reproduction technique. After obtaining a sperm sample, a sperm suspension is prepared and sperm concentration determined. After following the aforementioned process steps for binding mature sperm to a suitable mature sperm binding substrate, the proportion of mature sperm in the sample is determined. If the proportion of mature sperm is at a predetermined minimum level, or within a predetermined range, an appropriate assisted reproduction technique may be recommended and attempted. For example, if the total motile sperm is <1,000,000, the procedure to follow is IVF, and if the total motile sperm concentration is <100,000, the procedure which most likely will succeed is ICSI.

EXAMPLE

An examination was made whether (a) motile and immotile sperm would bind to Hylan (a modified HA gel) and (b) whether the Hylan-bound sperm fraction would be improved in cellular maturity and chromatin integrity measured by CK immunostaining and aniline blue chromatin staining. CK-immunocytochemistry detects cytoplasmic retention and thus diminished maturity of sperm. The aniline blue staining detects lysine-rich histones, a sign of chromatin immaturity and diminished decondensation ability in ejaculated sperm. From the point of view of intracytoplasmic sperm injection, it was also of particular interest whether the Hylan-bound non-motile sperm fractions would be enriched in viable spermatozoa.

Hylan was combined with tantalum, a heavy metal which is chemically inert and, unlike iron, does not affect the rate of destructive sperm lipid peroxidation. The Hylan/tantalum was prepared in the form of a gel and applied by a syringe as a coating to the center portion of a glass slide. A human sperm-containing suspension was also applied with a syringe to the glass slide, adjacent the Hylan/tantalum gel, so as to contact the Hylan/tantalum gel at the gel periphery. The slide was then viewed through a microscope at 100× to determine whether any sperm were bound to the gel at the periphery.

Sperm in the initial semen was compared with those attached to Hylan according to their staining pattern of mature (no or light CK staining indicating or minimal cytoplasmic retention), intermediate or immature (heavy or solid CK staining, indicating substantial cytoplasmic retention. Another aliquot of the same semen was attached to another HA coated bead and stained with aniline blue, which highlights immature chromatin in the sperm nucleus.

Figure 19:
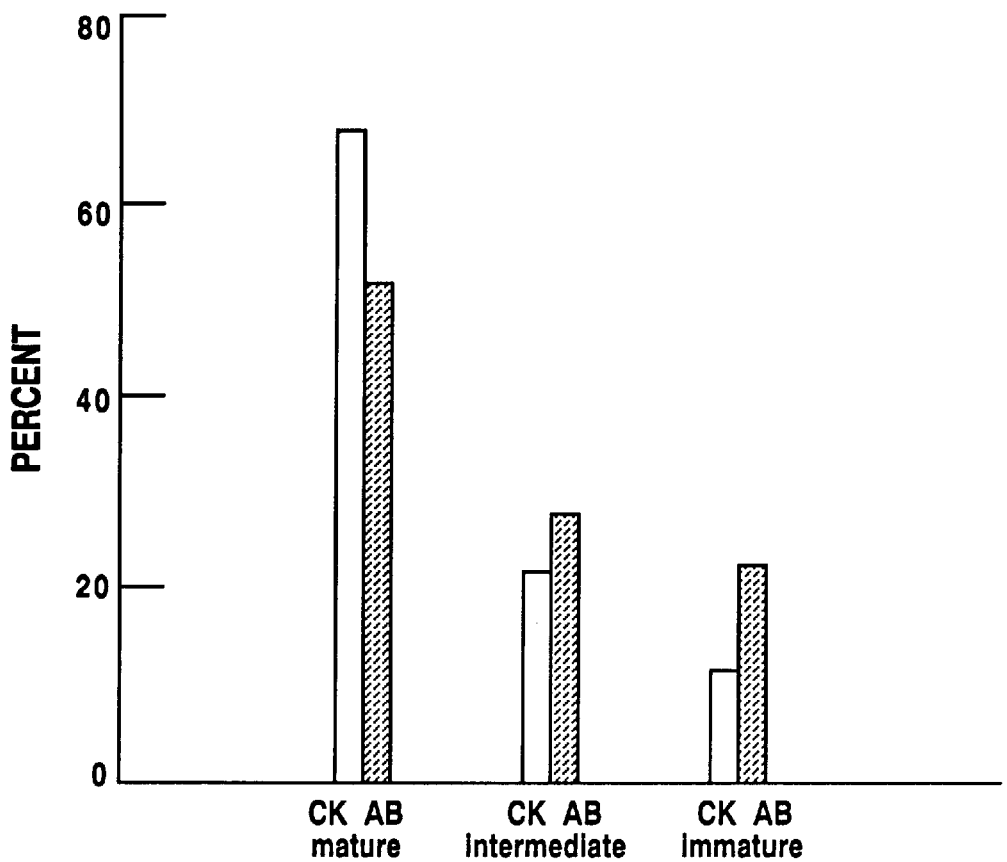
FIG. 19 is a graphical representation of the distribution of mature and immature sperm in a semen sample.
Figure 20:
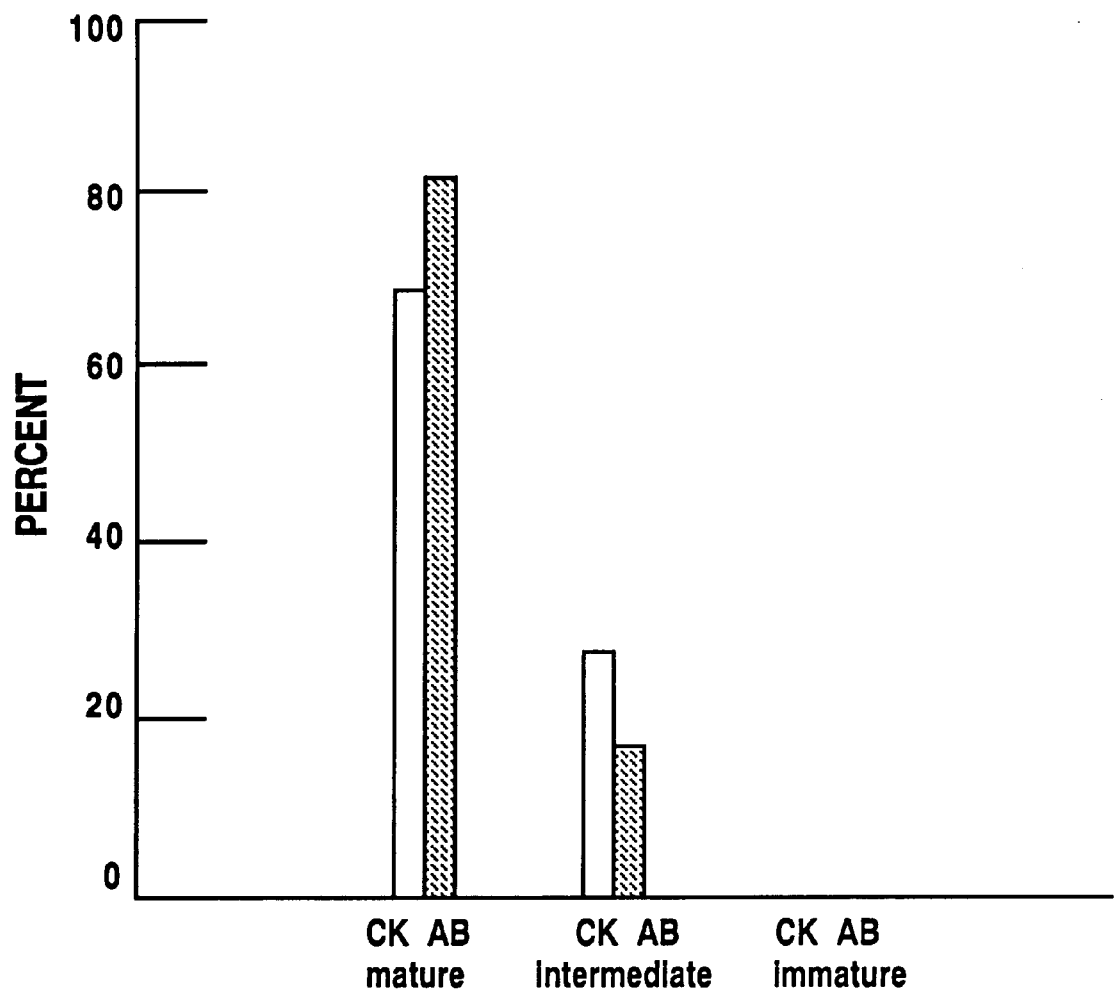
FIG. 20 is a graphical representation of the distribution of mature and immature sperm from the semen sample of FIG. 19, attached to a sperm binding substrate of the present invention.

The distribution of mature, intermediate and immature spermatozoa in semen samples and in their respective Hylan-bound sperm fractions is shown in FIGS. 19, and 20, respectively, which graphically depict 25 sample pairs, about 10,000 and 5,000 sperm scored, respectively. The results indicate that: 1) mature sperm with no cytoplasmic retention selectively bind to Hylan, 2) sperm fractions bound to Hylan showed a lower incidence of aniline blue staining, indicating improved sperm chromatin structure, 3) Hylan also attracts immotile spermatozoa from slowly agitated semen, 4) bound motile sperm maintain sustained flagellar activity similar to the motility in the control sperm fraction, 5) Hylan-bound fractions are also enriched in viable sperm (motile sperm which showed diminished Hoechst stain exclusion did not bind well to the gel) and 6) the HA facilitated the demonstration of another aspect: the relationship between HA binding and sperm maturity by both CK immunocytochemistry (retention of extra cytoplasm) and by aniline blue staining (chromatin immaturity).

Accordingly, it is believed that sperm selection by the process and system of the present invention is likely to yield higher per transfer pregnancy rates, and will have a protective effect by diminishing the propagation of defective genetic material.

Mature sperm selected in the manner utilized in the present invention gives lower rate of lipid peroxidation, which results in less DNA destruction and the potential for less cancer or other problems in children. Such sperm has improved genetic material with respect to lesser incidence of aneuploidies and better integrity and a lower extent of DNA cleavage. Selection of viable, non-motile sperm will be facilitated with the non-invasive method described in of the present invention.

While the present invention has been particularly described, in conjunction with a specific preferred embodiment, it is evident that many alternatives, modifications and variations will be apparent to those skilled in the art in light of the foregoing description. The key issue is that mature sperm have a surface membrane structure different from immature sperm. Thus, mature sperm with less aneuploidies, DNA cleavage and cytoplasmic retention may be selected based on the surface membrane properties of sperm. It is therefore contemplated that the appended claims will embrace any such alternatives, and mature sperm binding material coated surfaces of various embodiments, modifications and variations as falling within the true scope and spirit of the present invention.

Thus, having described the invention, what is claimed is:

1. A process for selecting mature sperm comprising the steps of:
   a) applying a binding substrate comprising hyaluronic acid or a salt thereof specific to mature sperm to a surface;

b) applying a sperm suspension to said surface;

c) contacting said sperm suspension and the mature sperm binding substrate on said surface;

d) permitting mature sperm from said sperm suspension to bind to said mature sperm binding substrate at a periphery thereof; and e) removing bound sperm from the periphery of said mature sperm binding substrate.

2. The process of claim 1 wherein said mature sperm binding substrate comprises a fluid.

3. The process of claim 1 wherein said sperm suspension and said mature sperm binding substrate are applied and contacted on the surface of a transparent structure.

4. The process of claim 3 further including the step of viewing the mature sperm bound to said mature sperm binding substrate by passing light through said transparent structure and said mature sperm binding substrate on said surface.

5. The process of claim 4 wherein said sperm suspension and said mature sperm binding substrate are applied and contacted on the surface of a glass slide.

6. The process of claim 1 wherein said mature sperm are removed from said mature sperm binding substrate by a micropipette.

7. The process of claim 1 further including the step of agitating said sperm suspension with respect to said mature sperm binding substrate on said surface.

8. The process of claim 1 further including the step of waiting a predetermined time between steps (c) and (e) to permit a portion of mature sperm bound to said mature sperm binding substrate to dis-bond from said mature sperm binding substrate.

9. The process of claim 1 including prior to step (e) the step of immobilizing said mature sperm bound to said mature sperm binding substrate.

10. The process of claim 1 including, prior to step (e) the step of using a micropipette to crush or at least partially remove tails of said mature sperm bound to said mature sperm binding substrate.

11. The process of claim 1 including prior to step (e), the steps of determining relative tail motion of sperm bound to said binding substrate and selecting for removal bound sperm having greater tail motion and activity.

12. The process of claim 1 wherein in step (d) motile and non-motile mature sperm bind to said mature sperm binding substrate.

13. The process of claim 1 further including the steps of:

f) washing the mature sperm removed from said mature sperm binding substrate; and g) injecting the washed sperm into an egg to attempt to fertilize said egg.

14. The process of claim 1 wherein said mature sperm binding substrate is not specific to immature sperm.

15. The process of claim 1 wherein said sperm suspension comprises human sperm.

16. The process of claim 1 wherein said sperm suspension comprises non-human mammalian sperm, including those of wild animals existing in zoos and of endangered species.

17. A process for selecting mature sperm comprising the steps of:

a) applying a fluid binding substrate specific to mature sperm comprising hyaluronic acid or a salt thereof to a surface, the mature sperm binding substrate being not specific to immature sperm;

b) applying a sperm suspension to said surface;

c) contacting said sperm suspension and the mature sperm binding substrate on said surface;

d) agitating said sperm suspension with respect to said binding substrate on said surface;

e) permitting motile mature sperm from said sperm suspension to bind to said mature sperm binding substrate at a periphery thereof;

f) waiting a predetermined time to permit non-motile, mature sperm to bind to said mature sperm binding substrate; and g) removing bound mature sperm from the periphery of said mature sperm binding substrate.

18. The process of claim 17 wherein said sperm suspension and said mature sperm binding substrate are applied and contacted on the surface of a structure transparent to the wavelength of light energy of the visualization system.

19. The process of claim 18 further including the step of viewing the mature sperm bound to said mature sperm binding substrate by passing light through said transparent structure and said mature sperm binding substrate on said surface.

20. The process of claim 17 wherein said mature sperm are removed from said mature sperm binding substrate by a micropipette.

21. The process of claim 17 further including the step of waiting a predetermined time between steps (c) and (g) to permit a portion of mature sperm bound to said mature sperm binding substrate to dis-bond from said mature sperm binding substrate.

22. The process of claim 17 including prior to step (e) the step of immobilizing said mature sperm bound to said mature sperm binding substrate.

23. The process of claim 17 including prior to step (g), the steps of determining relative tail motion of sperm bound to said binding substrate and selecting for removal bound sperm having greater tail motion and activity.

24. The process of claim 17 further including the steps of:

h) washing the mature sperm removed from said mature sperm binding substrate; and i) injecting the washed sperm into an egg to attempt to fertilize said egg.

25. The process of claim 17 wherein said sperm suspension comprises human sperm.

26. The process of claim 17 wherein said sperm suspension comprises non-human mammalian sperm.

27. A process for selecting mature sperm comprising the steps of:

a) contacting a sperm suspension and a binding substrate specific to mature sperm comprising hyaluronic acid or a salt thereof;

b) permitting mature sperm from said sperm suspension to bind to said mature sperm binding substrate at a periphery thereof;

c) immobilizing said mature sperm bound to said mature sperm binding substrate; and d) removing bound sperm from the periphery of said mature sperm binding substrate.

28. The process of claim 27 wherein said mature sperm binding substrate comprises a fluid.

29. The process of claim 27 wherein said sperm suspension and said mature sperm binding substrate are applied and contacted on the surface of a transparent structure.

30. The process of claim 29 further including the step of viewing the mature sperm bound to said mature sperm binding substrate by passing light through said transparent structure and said mature sperm binding substrate on said surface.

31. The process of claim 27 wherein said mature sperm are removed from said mature sperm binding substrate by a micropipette.

32. The process of claim 27 further including the step of agitating said sperm suspension with respect to said mature sperm binding substrate on said surface.

33. The process of claim 27 further including the step of waiting a predetermined time to permit a portion of mature sperm bound to said mature sperm binding substrate to dis-bond from said mature sperm binding substrate.

34. The process of claim 27 including, prior to step (d) the step of using a micropipette to crush or at least partially remove tails of said mature sperm bound to said mature sperm binding substrate.

35. The process of claim 27 including prior to step (d), the steps of determining relative tail motion and activity of sperm bound to said binding substrate and selecting for removal bound sperm having greater tail motion and activity.

36. The process of claim 27 further including the steps of:
  e) washing the mature sperm removed from said mature sperm binding substrate; and
  f) injecting the washed sperm into an egg to attempt to fertilize said egg.

37. The process of claim 27 wherein said sperm suspension comprises human sperm.

38. The process of claim 27 wherein said sperm suspension comprises non-human mammalian sperm.

39. A kit for selecting mature sperm comprising:
  a surface having coated on a portion thereof a mature sperm binding substrate comprising hyaluronic acid or a salt thereof, said surface adapted to receive a sperm suspension for contacting said mature sperm binding substrate and selectively binding mature sperm to said mature sperm binding substrate; and
  means for removing said sperm bound to said mature sperm receptor fluid.

40. The kit of claim 39 wherein the removing means comprises a micropipette.

41. The kit of claim 40 further including a micropipette for injecting removed mature sperm into an oocyte, the micropipette for removing the mature sperm having a larger diameter than the micropipette for injecting the removed mature sperm.

42. A kit for selecting mature sperm comprising:
  means for receiving a coating of a mature sperm binding substrate comprising hyaluronic acid or a salt thereof, the receiving means adapted to receive a sperm suspension for contacting said mature sperm binding substrate and selectively binding mature sperm to said mature sperm binding substrate; and
  means for removing said sperm bound to said mature sperm receptor fluid.

43. The kit of claim 42 wherein the removing means comprises a micropipette.

44. The kit of claim 42 wherein the receiving means comprises a transparent structure on which said sperm suspension and said mature sperm binding substrate are contacted.

45. The kit of claim 42 wherein the receiving means comprises a glass slide.

46. The kit of claim 45 wherein said glass slide has a depression therein for receiving said sperm suspension and said mature sperm binding substrate.

47. The kit of claim 42 wherein the receiving means comprises a projection on which said mature sperm binding substrate is at least partially coated.

48. The kit of claim 47 wherein said projection is straight.

49. The kit of claim 47 wherein said projection is helical.

50. The kit of claim 42 wherein the receiving means comprises a three dimensional structure to facilitate observation of multiple bound mature sperm.

51. The kit of claim 42 wherein the receiving means comprises a container having said mature sperm binding substrate coated on an inner surface thereof, and further including means for agitating said sperm suspension with respect to said mature sperm binding substrate.

52. The kit of claim 42 wherein the receiving means comprises a container having said mature sperm binding substrate coated in a strip on an inner surface thereof.

53. The kit of claim 42 wherein the receiving means comprises a mesh having said mature sperm binding substrate coated on at least a portion thereof.

54. The kit of claim 42 wherein the receiving means comprises a round structure having said mature sperm binding substrate coated on at least a portion of an outer surface thereof.

55. The kit of claim 42 wherein the receiving means comprises a projection on which said mature sperm binding substrate is at least partially coated, said projection being frangible to permit at least a portion of the coated projection to be observable by microscopic means and manipulated to remove mature sperm.

56. A process for determining the proportion of mature sperm in a sperm sample comprising the steps of:
  a) applying a mature sperm binding substrate comprising hyaluronic acid or a salt thereof to a surface;
  b) applying a sperm suspension of known concentration from said sperm sample to said surface;
  c) contacting said mature sperm binding substrate and said sperm suspension on said surface;
  d) permitting mature sperm from said sperm suspension to bind to said mature sperm binding substrate at a periphery thereof; and
  e) determining the proportion of mature sperm from said sperm suspension bound to said mature sperm binding substrate.

57. The process of claim 56 further including the step of contacting the mature sperm bound to said mature sperm binding substrate with a toxin to said mature sperm.

58. The process of claim 56 further including the steps of determining if a predetermined minimum proportion of mature sperm is present in said sample, and determining if the donor of said sperm sample is suitable for assisted reproduction procedures.

59. The process of claim 58 further including the step of determining the most suitable assisted reproduction technique for said donor based on the proportion of mature sperm present in said sample.

60. A kit for determining the proportion of mature sperm in a sperm sample comprising:
  a surface having coated on a portion thereof a mature sperm binding substrate comprising hyaluronic acid or a salt thereof, said substrate adapted to receive a sperm suspension for contacting said mature sperm binding substrate and selectively binding mature sperm to said mature sperm binding substrate; and
  means for determining proportion of said sperm bound to said mature sperm binding substrate.

61. The kit of claim 60 wherein the determining means comprises a microscope.

62. The kit of claim 60 wherein the determining means comprises a video system for analysis of sperm tail dynamics.

63. The process of claim 1 wherein said mature sperm binding substrate comprises a fluid and further including, prior to step (e), the step of agitating said sperm suspension with respect to said mature sperm binding substrate on said surface.

64. The process of claim 63 further including, prior to step (e), the step of viewing the mature sperm bound to said mature sperm binding substrate.

65. The process of claim 64 wherein step (e) comprises removing the mature sperm from said mature sperm binding substrate with a micropipette.

66. The process of claim 65 wherein said sperm suspension and said mature sperm binding substrate are applied and contacted on the surface of a transparent structure.

67. The process of claim 66 further including the steps of:
 f) washing the mature sperm removed from said mature sperm binding substrate; and
 g) injecting the washed sperm into an egg to attempt to fertilize said egg.

68. The process of claim 66 further including, prior to step (e), the step of immobilizing said mature sperm bound to said mature sperm binding substrate.

69. The process of claim 68 further including step (f) washing the mature sperm removed from said mature sperm binding substrate.

70. The process of claim 69 further including step (g) injecting the mature sperm into an oocyte.

* * * * *

UNITED STATES PATENT AND TRADEMARK OFFICE
CERTIFICATE OF CORRECTION

PATENT NO. : 5,897,988
DATED : April 27, 1999
INVENTOR(S) : Gabor B. Huszar

It is certified that error appears in the above-identified patent and that said Letters Patent is hereby corrected as shown below:

In column 6, line 48, after "the" delete "act" and substitute therefor - - fact - -.

In column 7, line 11, after "developing" delete "mbryo" and substitute therefor - - embryo - -.

In column 7, line 47, delete "36° C." and substitute therefor - - 36° C - -.

In column 7, line 50, delete "albumine" and substitute therefor - - albumin - -.

In column 10, line 7, delete "and" after "68a".

Signed and Sealed this

Twelfth Day of October, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,897,988
DATED : April 27, 1999
INVENTOR(S) : Gabor Huszar

It is certified that error appears in the above-identified patent and that said Letters Patent is hereby corrected as shown below:

<u>Column 1,</u>
Lines 5-7, please insert the following paragraph:
-- This invention was made with United States Government support under Grant No. HD32902 from the National Institute of Health ("NIH"). The United States Government has certain rights in this invention. --

Signed and Sealed this

Tenth Day of August, 2004

JON W. DUDAS
*Acting Director of the United States Patent and Trademark Office*